(12) United States Patent
Casterlin et al.

(10) Patent No.: US 9,005,991 B2
(45) Date of Patent: Apr. 14, 2015

(54) DEVICE AND METHOD FOR TESTING BIOLOGICAL SAMPLES

(75) Inventors: Douglas Casterlin, Hillsdale, NY (US); Larry Ferringo, Turnersville, NJ (US)

(73) Assignee: American Bio Medica Corporation, Kinderhook, NY (US)

( * ) Notice: Subject to any disclaimer, the term of this patent is extended or adjusted under 35 U.S.C. 154(b) by 771 days.

(21) Appl. No.: 13/343,854

(22) Filed: Jan. 5, 2012

(65) Prior Publication Data

US 2013/0177996 A1 Jul. 11, 2013

(51) Int. Cl.
 *G01N 33/558* (2006.01)
 *G01N 21/75* (2006.01)
 *B01L 3/00* (2006.01)

(52) U.S. Cl.
 CPC ............ *G01N 33/558* (2013.01); *B01L 3/5023* (2013.01); *B01L 2200/025* (2013.01); *B01L 2300/043* (2013.01); *B01L 2300/0654* (2013.01); *B01L 2300/0825* (2013.01); *B01L 2300/0874* (2013.01); *B01L 2300/0861* (2013.01); *Y10S 435/805* (2013.01); *Y10S 435/81* (2013.01); *Y10S 435/97* (2013.01); *Y10S 436/81* (2013.01); *Y10S 436/815* (2013.01)

(58) Field of Classification Search
 CPC .................................................. G01N 33/558
 USPC .......... 422/401, 408, 420, 425, 430; 435/288.4, 288.5, 805, 810, 970; 436/514, 810, 815
 See application file for complete search history.

(56) References Cited

U.S. PATENT DOCUMENTS

| | | |
|---|---|---|
| 6,277,646 B1 | 8/2001 | Guirguis et al. |
| 6,406,922 B2 | 6/2002 | Casterlin et al. |
| 7,090,803 B1 | 8/2006 | Gould et al. |
| 7,205,159 B2 | 4/2007 | Cole et al. |
| 7,238,322 B2 | 7/2007 | Wang et al. |
| 7,241,417 B2 | 7/2007 | Lee et al. |
| 7,695,953 B2 | 4/2010 | Gould et al. |
| 2002/0048819 A1 | 4/2002 | Alley |
| 2002/0173047 A1 | 11/2002 | Hudak et al. |
| 2003/0129767 A1 | 7/2003 | Bautista et al. |
| 2003/0206829 A1 | 11/2003 | Cui et al. |
| 2004/0184954 A1 | 9/2004 | Guo et al. |
| 2005/0119589 A1 | 6/2005 | Tung et al. |
| 2005/0142031 A1 | 6/2005 | Wickstead et al. |
| 2006/0292035 A1 | 12/2006 | Gould et al. |
| 2007/0154350 A1 | 7/2007 | Wuske et al. |
| 2008/0145891 A1 | 6/2008 | Burton |
| 2009/0320623 A1 | 12/2009 | Matallana-Kielmann |
| 2010/0024530 A1 | 2/2010 | Hopkins, II |
| 2010/0124517 A1 | 5/2010 | Cortelazzo |

FOREIGN PATENT DOCUMENTS

| | | |
|---|---|---|
| WO | WO-2004/038364 | 5/2004 |
| WO | WO-2007/026814 | 3/2007 |

OTHER PUBLICATIONS

European Search Report Regarding EP12150239.7.

*Primary Examiner* — Chris L Chin
(74) *Attorney, Agent, or Firm* — B. Aaron Schulman, Esq.; Stites & Harbison, PLLC.

(57) ABSTRACT

Devices and methods for testing a biological sample for an analyte of interest are provided that make use of a reaction chamber for receiving a reaction mixture, a housing positioned below the reaction chamber for receiving a test cassette, and a door that is positioned in the top portion of the housing. The door includes a ramp that extends downwardly into the housing such that biasing the ramp upwards opens the door into the cavity of the reaction chamber and places the reaction chamber in fluid communication with the insertion area to thereby allow the reaction mixture to flow onto a test cassette and allow for the determination of an amount of an analyte of interest.

31 Claims, 11 Drawing Sheets

DEVICE AND METHOD FOR TESTING BIOLOGICAL SAMPLES

FIELD OF THE INVENTION

The present invention relates in general to a device and method for testing biological samples for an analyte of interest. More particularly, the present invention relates to a device and method for testing biological samples, such as blood, plasma, serum, urine, or saliva samples, that makes use of a reaction chamber and a housing that can be placed in fluid communication with one another and used to create a convenient platform for mixing, incubating, and depositing a reaction mixture onto a test strip in a test cassette.

BACKGROUND OF THE INVENTION

Immunoassay devices that make use of immunochromatography are often utilized as a means to test a biological sample for the presence of an analyte of interest, such as a drug of abuse. For example, in many of these immunoassay devices and methods, a specified volume of a biological sample can be contacted with one end of a test strip that contains a colored reagent and that also contains an antigen or antibody dried to the test strip in discrete zones. In this regard, as the biological sample is wicked up by the test strip, the analyte in the sample reacts with the antigens or antibodies and any reactions, if present, can then simply be observed by the appearance or non-appearance of color in the discrete zones.

Given the relative ease with which the immunoassay results can be read, a number of immunoassay devices and methods have been developed to date that allow for the rapid screening of drugs of abuse or other analytes of interest in biological fluids. Many of these prior immunoassay devices and methods, however, have required significant pre-treatment steps where the biological sample must first be modified with specific reagents to dilute or denature any interferents, to modify the analyte structure, and/or to release the analyte from binding molecules prior to adding the biological sample to the testing device. Additionally, in many of these prior devices and methods, once the test sample is introduced, there has been no control provided over either the speed or the timing of the subsequent immunoassay reactions. Indeed, in a number of the prior devices and methods, the quantity of the reaction mixture placed in the testing device is the major factor that determines the speed and timing of all of the subsequent reactions and, in many instances, this ultimately leads to an inefficient or inaccurate result.

Accordingly, a device and method for testing a biological sample for an analyte of interest, such as a drug of abuse, that allows for not only control over the biological sample being tested, but that also allows for the quick and accurate testing of drugs of abuse or other analytes of interest would be both highly-desirable and beneficial.

SUMMARY OF THE INVENTION

It is thus an object of the present invention to provide a quick and accurate device and method for testing for an analyte of interest in a variety of biological samples, such as blood, plasma, serum, urine, or saliva samples, in a controlled manner.

These and other objects are provided by virtue of the present invention which comprises devices and methods for testing biological samples for an analyte of interest. In one exemplary embodiment of the present invention, a device for testing a biological sample is provided that includes a first reaction chamber and a second reaction chamber, where each reaction chamber has an interior wall that defines an open top of each reaction chamber and that further defines a cavity for receiving a reaction mixture. The device further includes a housing that is positioned below the first reaction chamber and the second reaction chamber. The housing includes a top portion, a bottom portion, a back wall, and two opposing side walls that define an open end of the housing as well as an interior insertion area that is designed to receive a test cassette containing a test strip for determining an amount of the analyte of interest in the biological sample.

To facilitate the contacting of the test strip with the reaction mixture, which includes the biological sample being tested, a pair of doors are positioned in the top portion of the housing, and each door includes a ramp that extends downwardly into the insertion area of the housing. In this regard, when the ramp is biased upward, such as by the insertion of the test cassette into the insertion area of the housing, the doors are opened into the cavity of their respective reaction chambers and the reaction chambers are placed in fluid communication with the insertion area. In certain embodiments of the devices of the present invention, each door includes a perimeter portion that is configured to easily separate from the top portion of the housing when each ramp is biased upward. In some embodiments, to further facilitate the opening of the doors, each ramp includes a front edge that is angled away from the open end of the housing such that, as a test cassette is inserted into the insertion area, the test cassette progressively engages the angled front edge of each ramp and progressively pushes the doors upward into each reaction chamber.

To prevent a test cassette from being prematurely inserted too far into the insertion area of the housing and prematurely contacting the ramps on the doors of the housing, and to also secure a test cassette in the insertion area, a pair of stops are further included in the housing. Generally, the stops are positioned on the top portion of the housing and extend downwardly into the insertion area such that the stops initially provide some resistance to the insertion of the test cassette, but then suitably engage a portion of the test cassette and secure it within the insertion area as the test cassette is fully inserted. In some embodiments, a guide is also attached to each side wall of the housing and is used to further secure the test cassette within the housing, while also preventing the test cassette from being inserted too far into the housing and prematurely contacting the ramps on the doors of the housing. In some embodiments, the guides are additionally used to align the reaction wells of the test cassettes underneath the doors such that, upon opening the doors into the cavities of their respective reaction chambers and placing the reaction chambers in fluid communication with the insertion area, the reaction mixtures flow down directly into the reaction wells of the test cassette.

With regard to the test cassette itself, each test cassette generally includes: a top cover that defines two reaction wells for receiving the reaction mixture from the reaction chambers and two windows for reading test results; a base that is configured to attach to the top cover; and at least one test strip that is interposed between the top cover and the base. As noted above, the two reaction wells are typically positioned on the top cover such that each reaction well can be aligned with each door in the top portion of the housing to allow the reaction mixture to flow directly into each reaction well upon opening the doors. To facilitate the flow of the reaction mixture into the reaction wells, in some embodiments, the top cover further includes a bridge that is positioned across each reaction well and provides support for the ramp upon the insertion of the test cassette into the insertion area. In this regard, instead of the ramp falling into the reaction well when the test cassette is inserted into the insertion area, the bridges allow the ramps to remain biased upward and the doors to remain open such that the reaction mixture can continue to flow into each reaction well upon the insertion of the cassette.

To further facilitate the testing of a biological sample using the device of the present invention, in certain embodiments, a cap is further provided for covering the open top of the first reaction chamber and the open top of the second reaction chamber. In some embodiments, the cap is connected to the housing by a flexible arm. In certain embodiments, the flexible arm includes a notch that is positioned in the flexible arm such that bending the flexible arm at the notch allows the cap to be aligned with the open top of the first reaction chamber and the open top of the second reaction chamber. Once the cap is aligned with the top of the reaction chambers, the cap can then be easily placed down onto the reaction chambers and secured to the reaction chamber by various means to allow for the mixing and/or incubating of a biological sample and one or more reagents as part of a particular test for an analyte of interest.

Further provided by the present invention are methods for testing a biological sample for an analyte of interest. In one exemplary implementation of a method for testing a biological sample for an analyte of interest, a device of the present invention is first provided that includes: a reaction chamber having an interior wall defining an open top and a cavity for receiving a reaction mixture; a housing positioned below the reaction chamber, and having a top portion, a bottom portion, a back wall, and two opposing side walls defining an open end and an insertion area for receiving a test cassette; and a door that is positioned in the top surface of the housing and includes a ramp that extends downwardly into the insertion area.

Subsequent to the providing the device, a biological sample and one or more reagents are placed into the cavity to thereby create a desired reaction mixture. Then, following a suitable mixing and/or incubation period that, in certain embodiments, can be facilitated by the placement of a cap over the open top of the reaction chamber, an immunoassay test cassette is inserted into the insertion area such that the test cassette biases the ramp upwards and opens the door into the cavity of the reaction chamber. Once the door is opened, the reaction mixture is then allowed to flow into the reaction well of each test cassette and onto an immunoassay test strip. Then, the results of the test are read and an amount of the analyte of interest in the biological sample is determined by analyzing the results through the windows in the test cassette. In some embodiments, and as indicated above, the methods of the present invention are useful for determining the amounts of a drug of abuse, including, but not limited to, amphetamines, benzodiazepines, cocaine, methadone, methamphetamines, phencyclidine, and tetrahydrocannabinol, in a biological sample.

Each of these embodiments and implementations of the devices and methods of the present invention, as well as other alternatives and modifications within the spirit and scope of the presently-disclosed invention, will become readily apparent to those of ordinary skill in the art after a study of the description and Figures in this document.

BRIEF DESCRIPTION OF THE DRAWING FIGURES

Figure 5A:
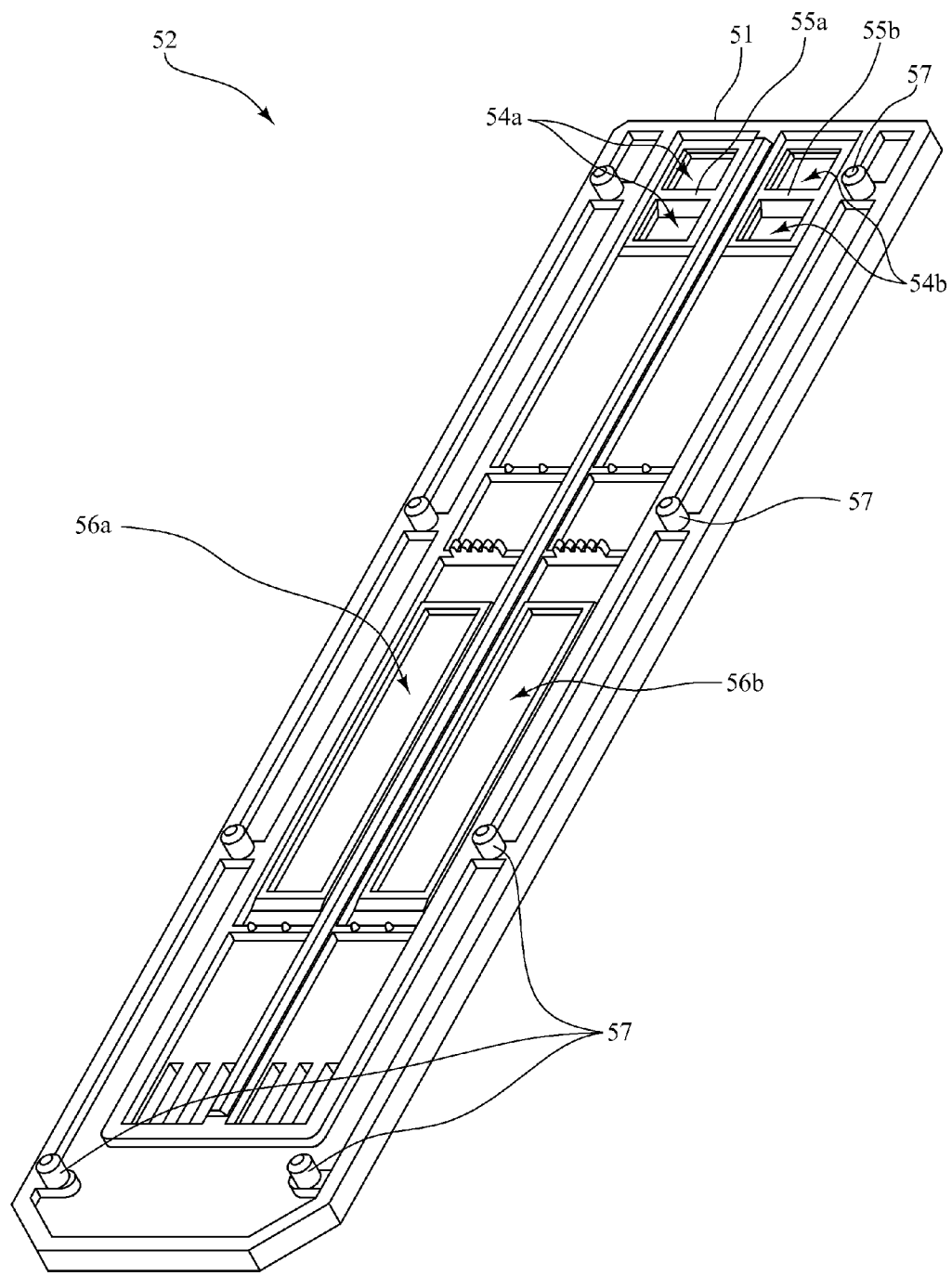
Figure 5B:
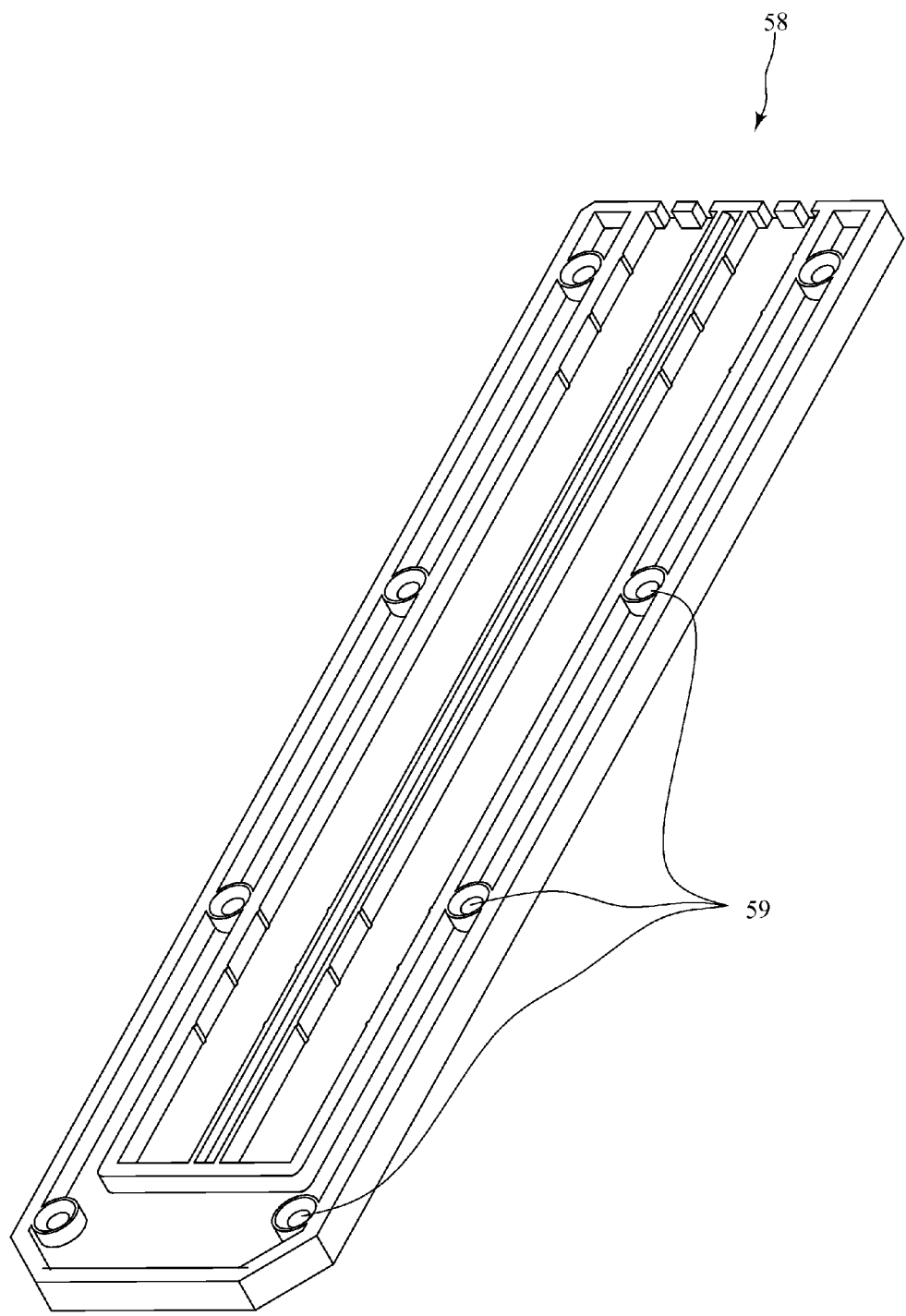
Figure 6A:
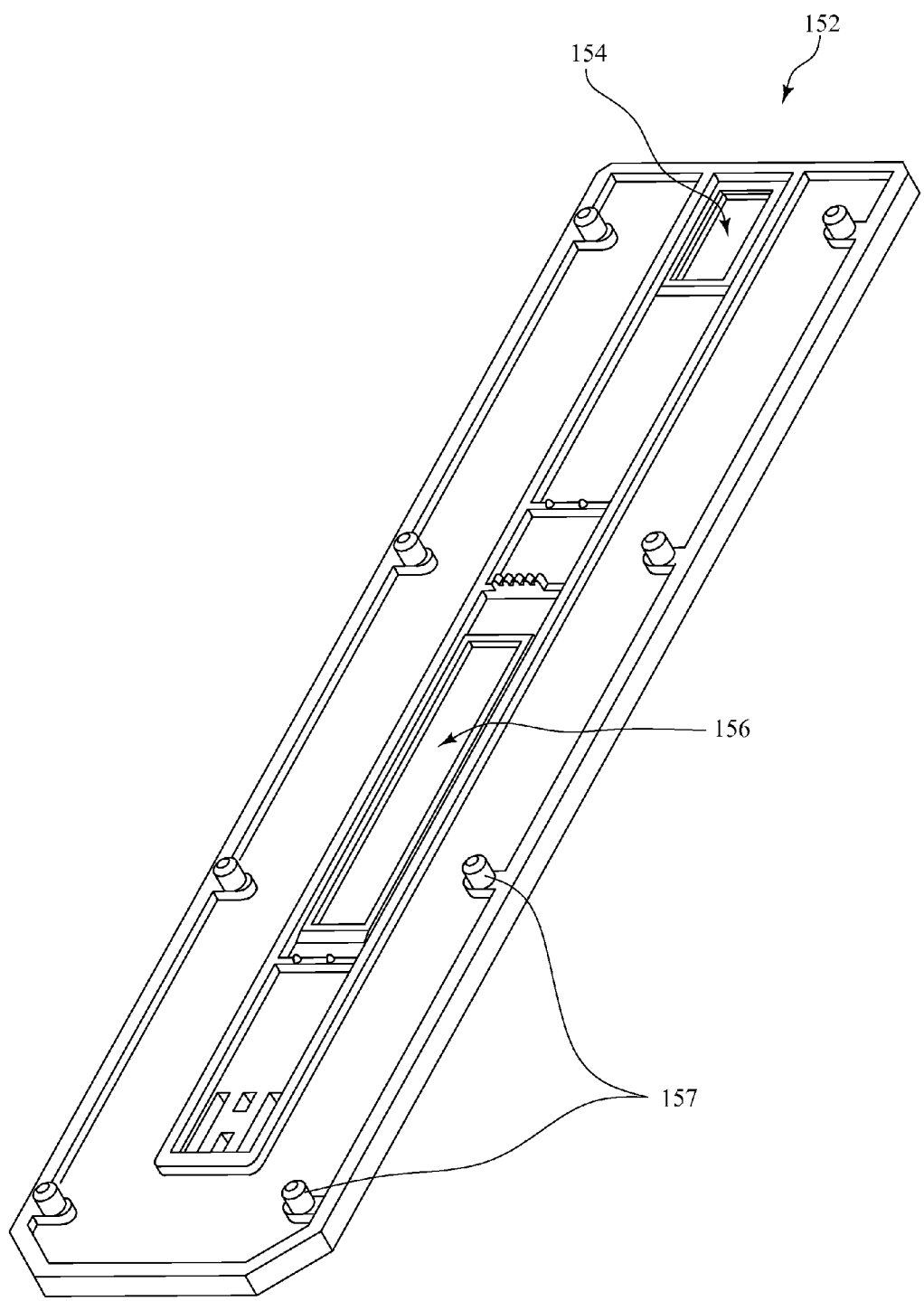
Figure 6B:
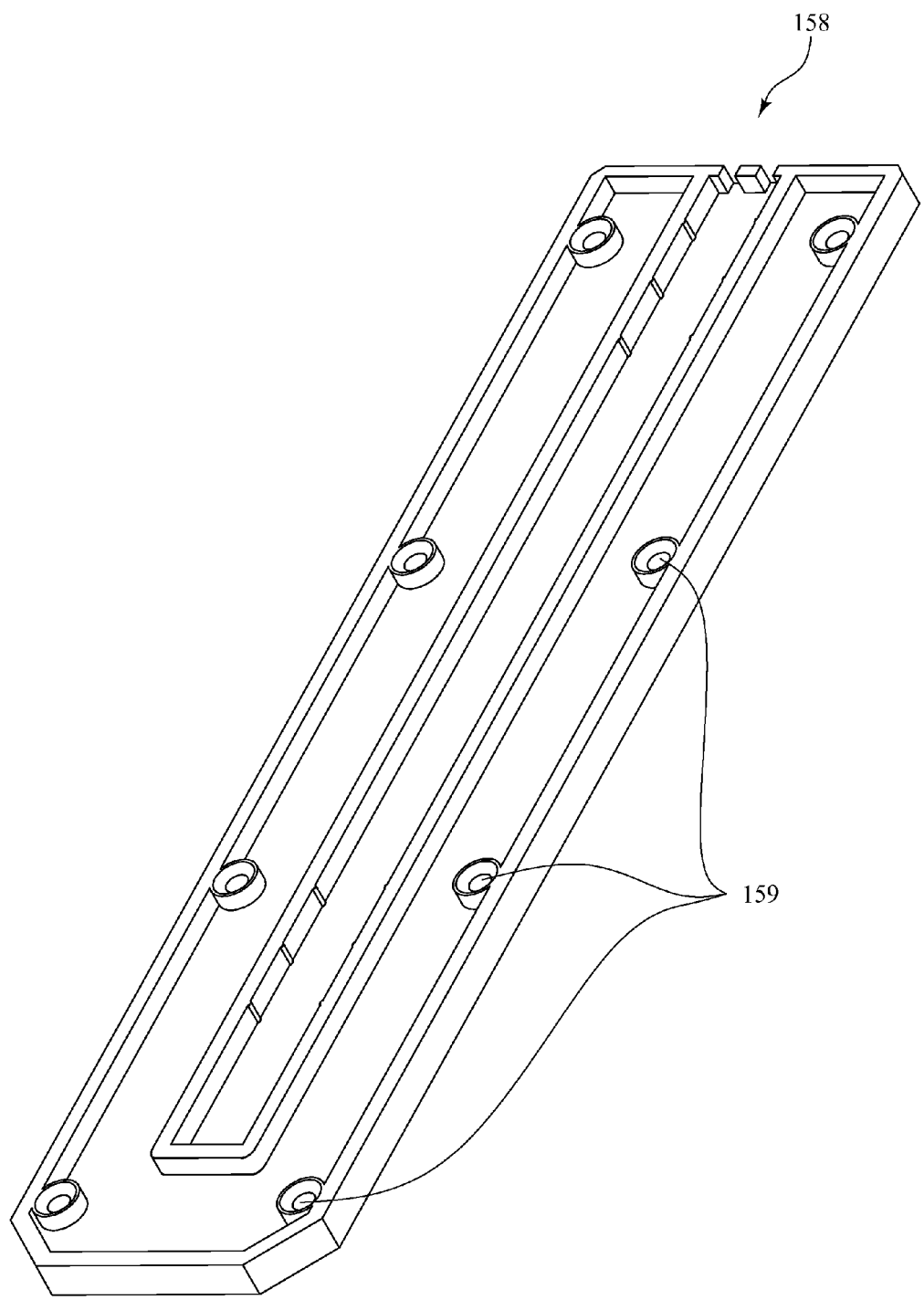
Figure 7:
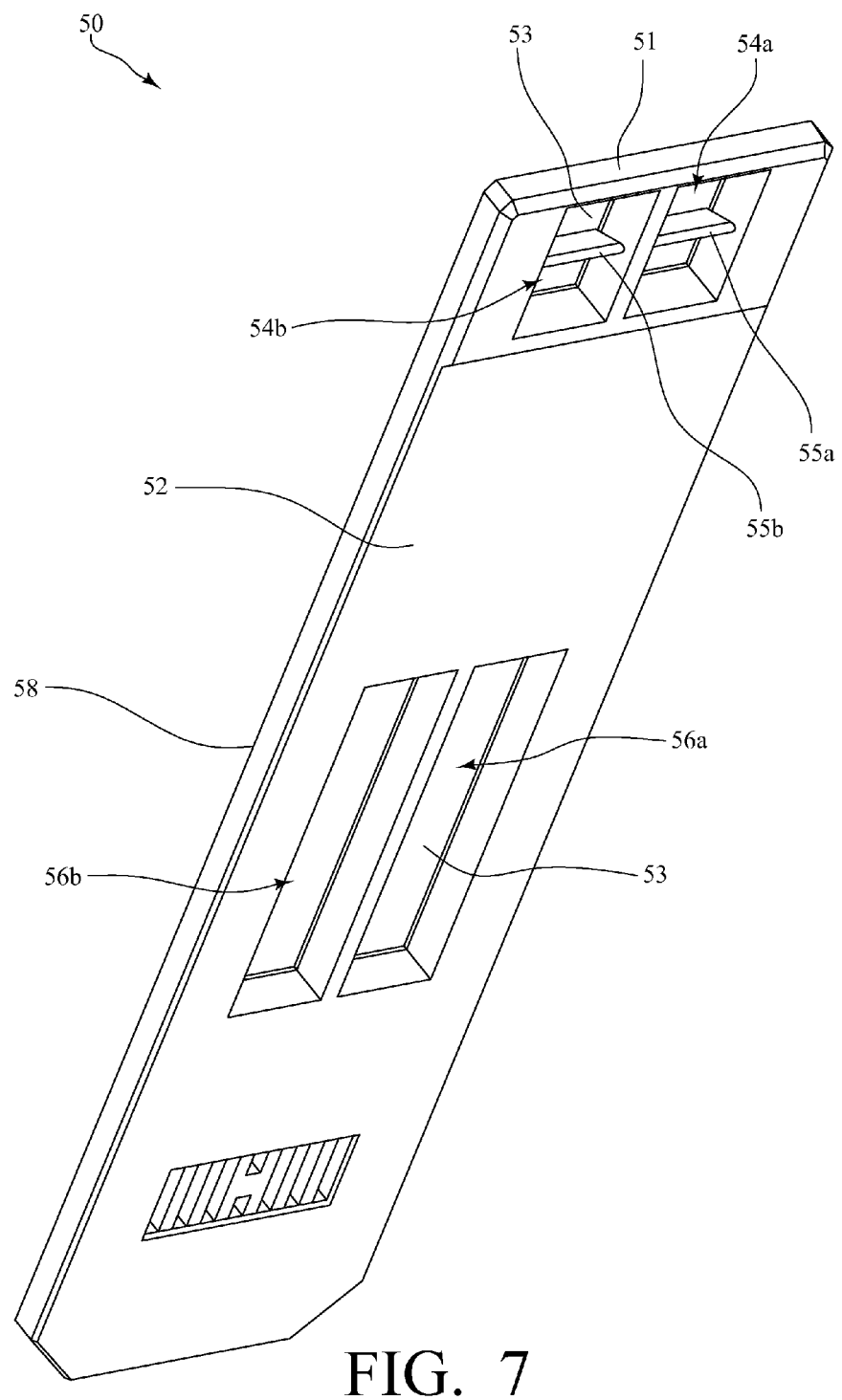
Figure 8:
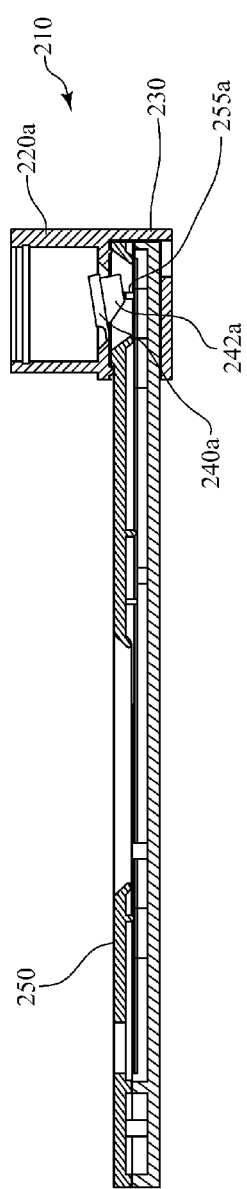
Figure 9:
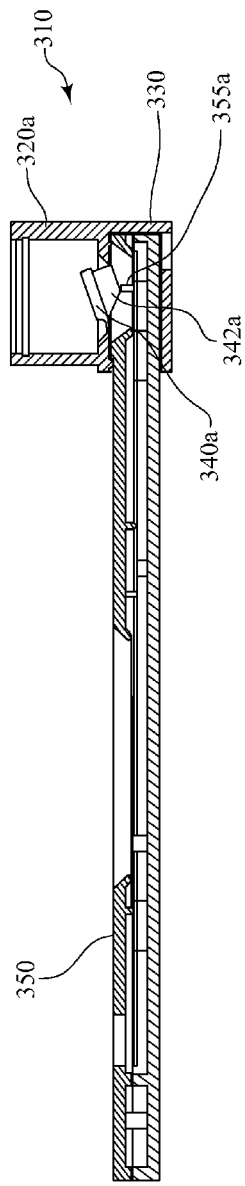
Figure 10:
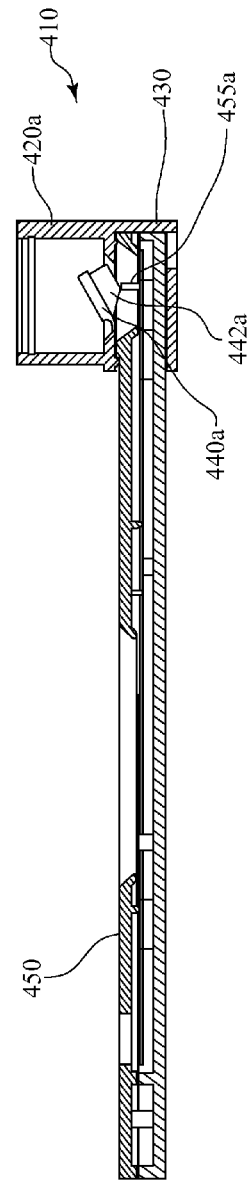
Figure 11:
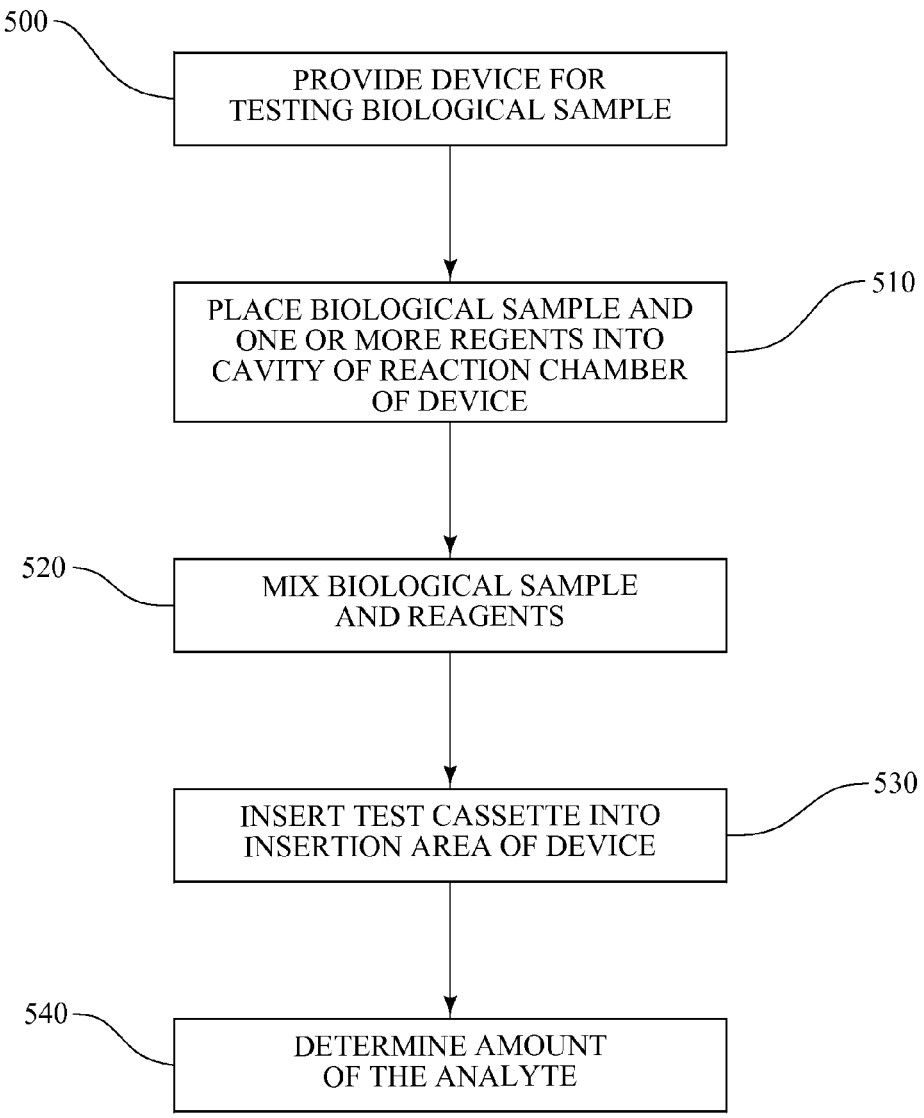

FIGS. 5A-5B include perspective views of a top cover (FIG. 5A) and a base (FIG. 5B) of an exemplary test cassette used in accordance with the present invention;

FIGS. 6A-6B include perspective views of a top cover (FIG. 6A) and a base (FIG. 6B) of an alternative exemplary test cassette used in accordance with the present invention;

FIG. 7 is another perspective view of the exemplary test cassette shown in FIGS. 5A-5B, but further illustrating the top cover and the base attached to one another with a test strip interposed between the top cover and the base;

FIG. 8 is a cross-sectional view of another device for testing biological samples made in accordance with the present invention, and illustrating a test cassette that includes a bridge with a low height inserted into the insertion area of the housing of the device;

FIG. 9 is a cross-sectional view of yet another device for testing biological samples made in accordance with the present invention, and illustrating a test cassette that includes a bridge with an intermediate height inserted into the insertion area of the housing of the device;

FIG. 10 is a cross-sectional view of a further device for testing biological samples made in accordance with the present invention, and illustrating a test cassette that includes a bridge with a high height inserted into the insertion area of the housing of the device; and FIG. 11 is a flow chart illustrating the steps included in an exemplary method for testing a biological sample for an analyte of interest in accordance with the present invention.

DETAILED DESCRIPTION OF THE PREFERRED EMBODIMENTS

In accordance with the present invention, devices and methods for testing a biological sample are provided. In particular, the present invention provides devices and methods for testing biological samples, such as blood, plasma, serum, urine, or saliva samples, that make use of a reaction chamber and a housing that can be placed in fluid communication with one another and used to create a convenient platform for mixing, incubating, and depositing a reaction mixture onto test strip in a test cassette.

Referring first to FIGS. 1-4, an exemplary device 10 for testing a biological sample for an analyte of interest in accordance with the present invention includes a first reaction chamber 20a and a second reaction chamber 20b. Each reaction chamber 20a, 20b includes an interior wall 22a, 22b that defines an open top 24a, 24b of each reaction chamber 20a, 20b and further defines a cavity 26a, 26b within each reaction chamber 20a, 20b for receiving a reaction mixture, as described in further detail below. In the device 10, each interior wall 22a, 22b is continuous such that the cavity 26a, 26b defined by each interior wall 22a, 22b is substantially cylindrical in shape. Of course, to the extent it may be desired, reaction chambers having various other shapes and sizes can be provided for a particular application or device without departing from the spirit and scope of the present invention. Similarly, although the device 10 includes a first reaction chamber 20a and a second reaction chamber 20b, it is, of course, contemplated that an exemplary device can be provided with any number of reaction chambers without departing from the spirit and scope of the present invention. For example, it is contemplated that a device for testing a biological sample can be provided in accordance with the present invention where the device includes a single reaction chamber or includes three or more reaction chambers.

Regardless of the number of reaction chambers included in an exemplary device, however, and referring now to FIGS. 1-4 and FIG. 7, the device 10 further includes a housing 30 that is positioned below the first reaction chamber 20a and the second reaction chamber 20b. The housing 30 includes a top portion 31, a bottom portion 32, a back wall 33, and two opposing side walls 34, 35 that define an open end 36 and an insertion area 37 for receiving a test cassette 50 including reaction wells 54a, 54b, as also described in further detail below. Additionally, the housing 30 includes a pair of doors 40a, 40b that are positioned in the top portion 31 of the housing 30. Each door 40a, 40b includes a ramp 42a, 42b that extends downwardly into the insertion area (e.g., in a direction perpendicular to the doors 40a, 40b). In this regard, when each ramp 42a, 42b is biased upward, such as by the insertion of the test cassette 50 into the insertion area 37, the doors 40a, 40b are opened into the cavities 26a, 26b of their respective reaction chambers 20a, 20b and the reaction chambers 20a, 20b are placed in fluid communication with the insertion area 37.

To facilitate the opening of the doors 40a, 40b, each door 40a, 40b further includes a perimeter portion 44a, 44b that is configured to separate from the top portion 31 of the housing 30 when each ramp 42a, 42b is biased upwards and the doors 40a, 40b are opened. For example, in certain embodiments, during the construction of the devices for testing a biological sample, the perimeter portions 44a, 44b of the doors 40a, 40b can be molded from a very thin section of material such that only a small amount of force needs to be applied to the ramps 42a, 42b to separate the doors 40a, 40b from the remainder of the top portion 31 of the housing 30 at the location of the perimeter portions 44a, 44b.

To further facilitate the opening of the doors 40a, 40b of the device 10, each ramp 42a, 42b includes a front edge 45a, 45b that is angled away from the open end 36 of the housing 30. By angling the front edges 45a, 45b away from the open end 36 of the housing 30, the triangular-shaped ramps 42a, 42b are thus configured such that, as a test cassette 50 is inserted into the insertion area 37, the test cassette 50 progressively engages the angled front edge 45a, 45b of each ramp 42a, 42b and progressively pushes the doors 40a, 40b upward into the reaction chambers 20a, 20b.

Figure 1:
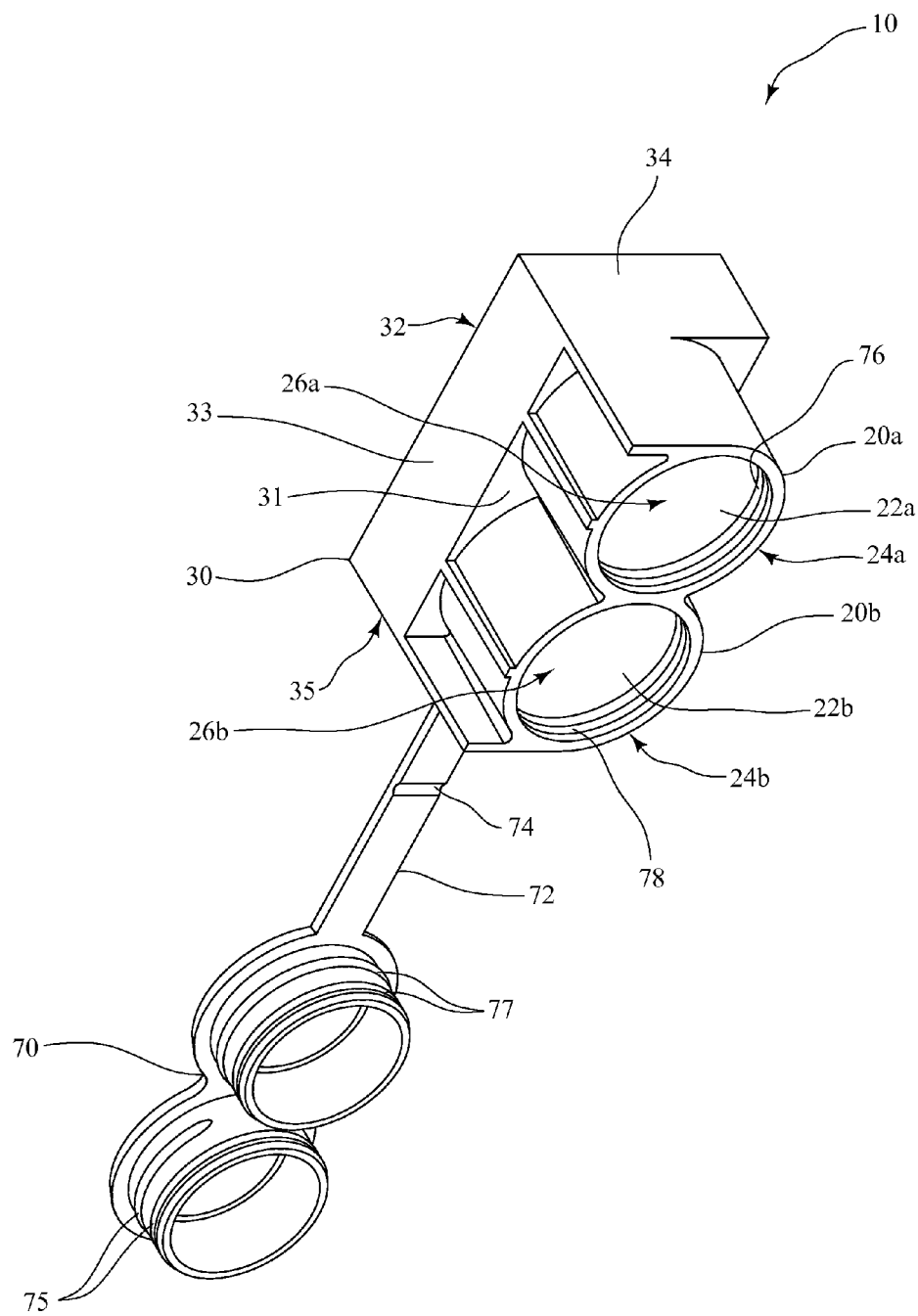
FIG. 1 is a perspective view of a device for testing biological samples made in accordance with the present invention.
Figure 2:
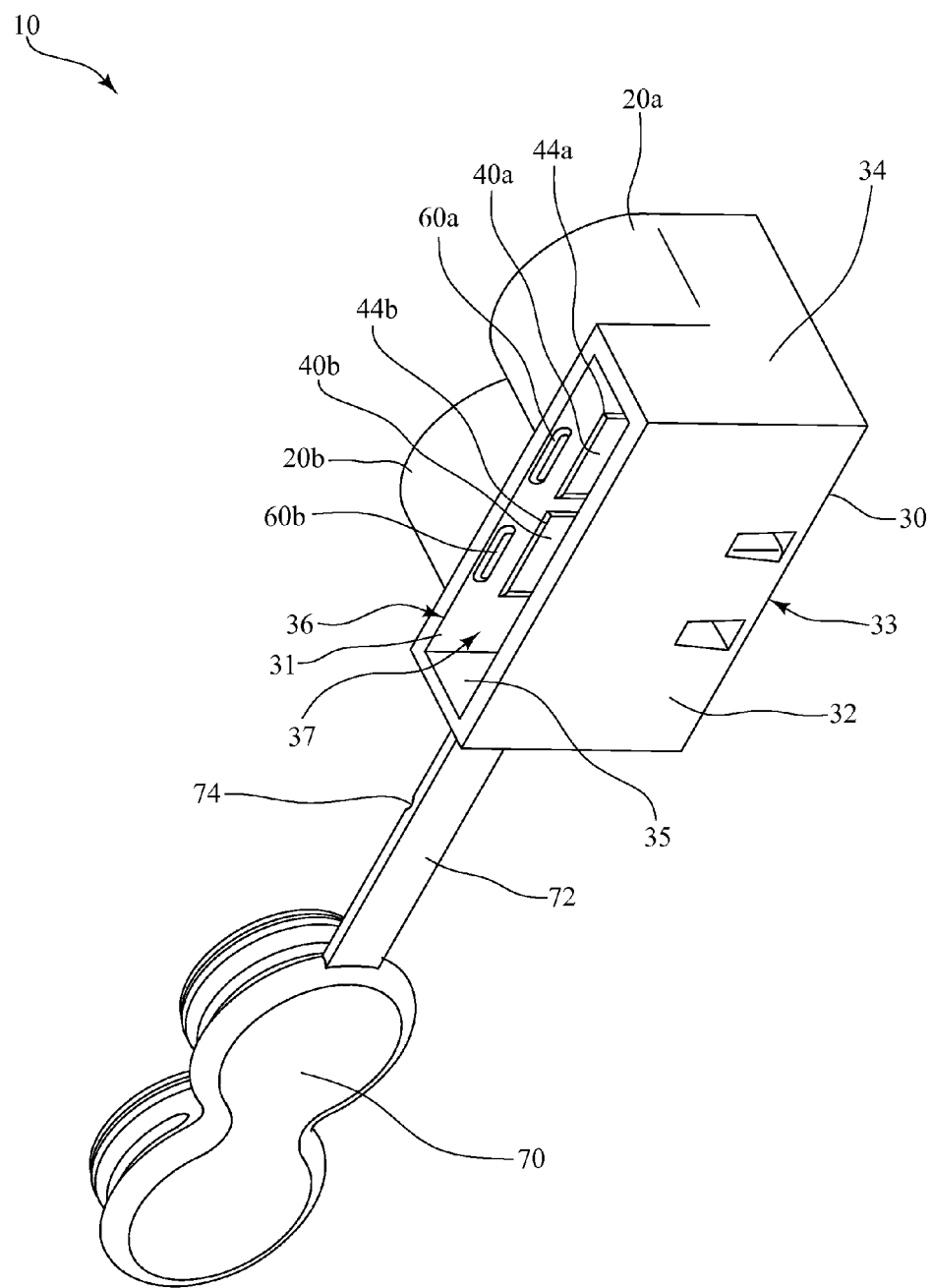
FIG. 2 is another perspective view of the device shown in FIG. 1, but further illustrating the bottom of the device.
Figure 3:
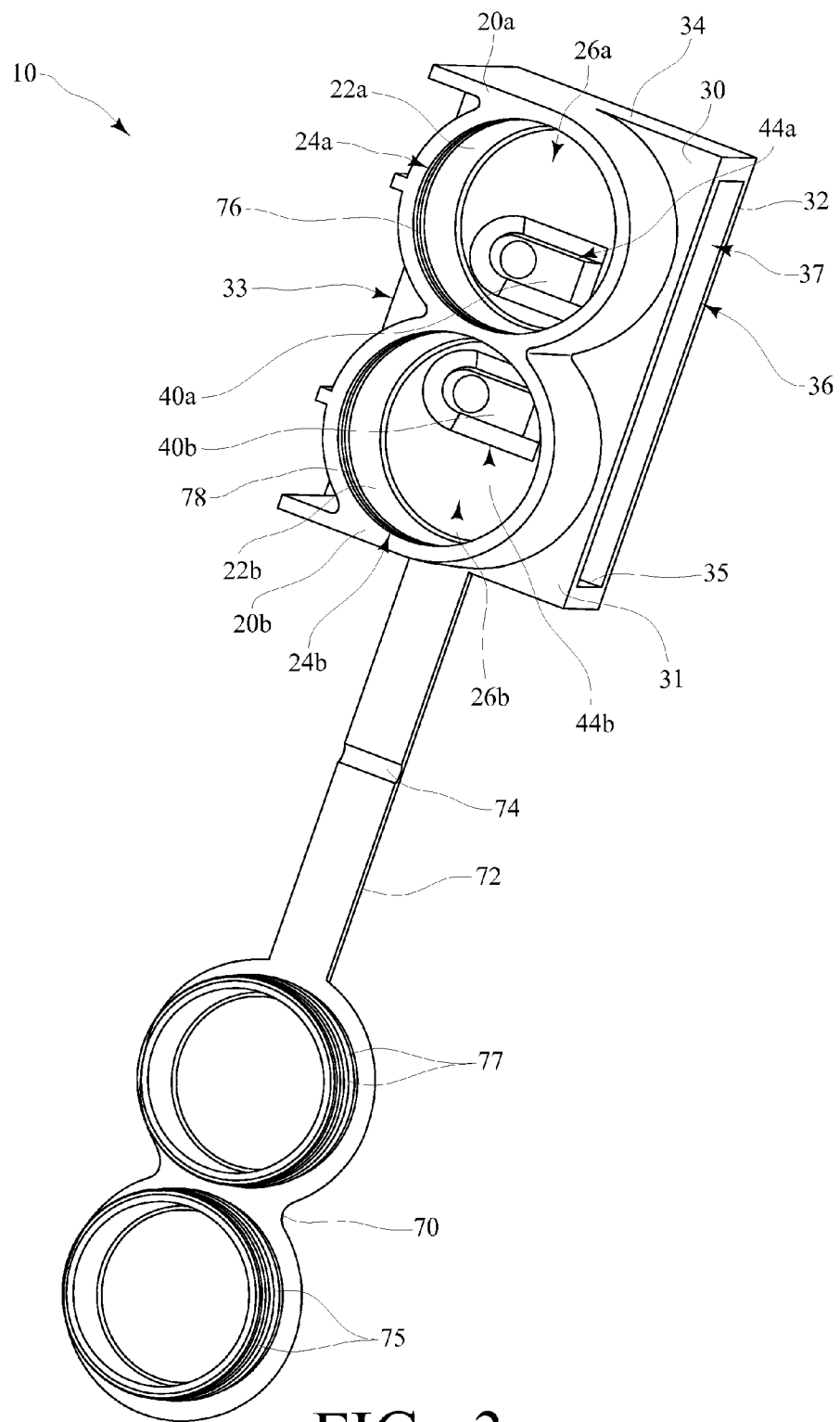
FIG. 3 is yet another perspective view of the device shown in FIG. 1, but further illustrating the top of the device.
Figure 4:
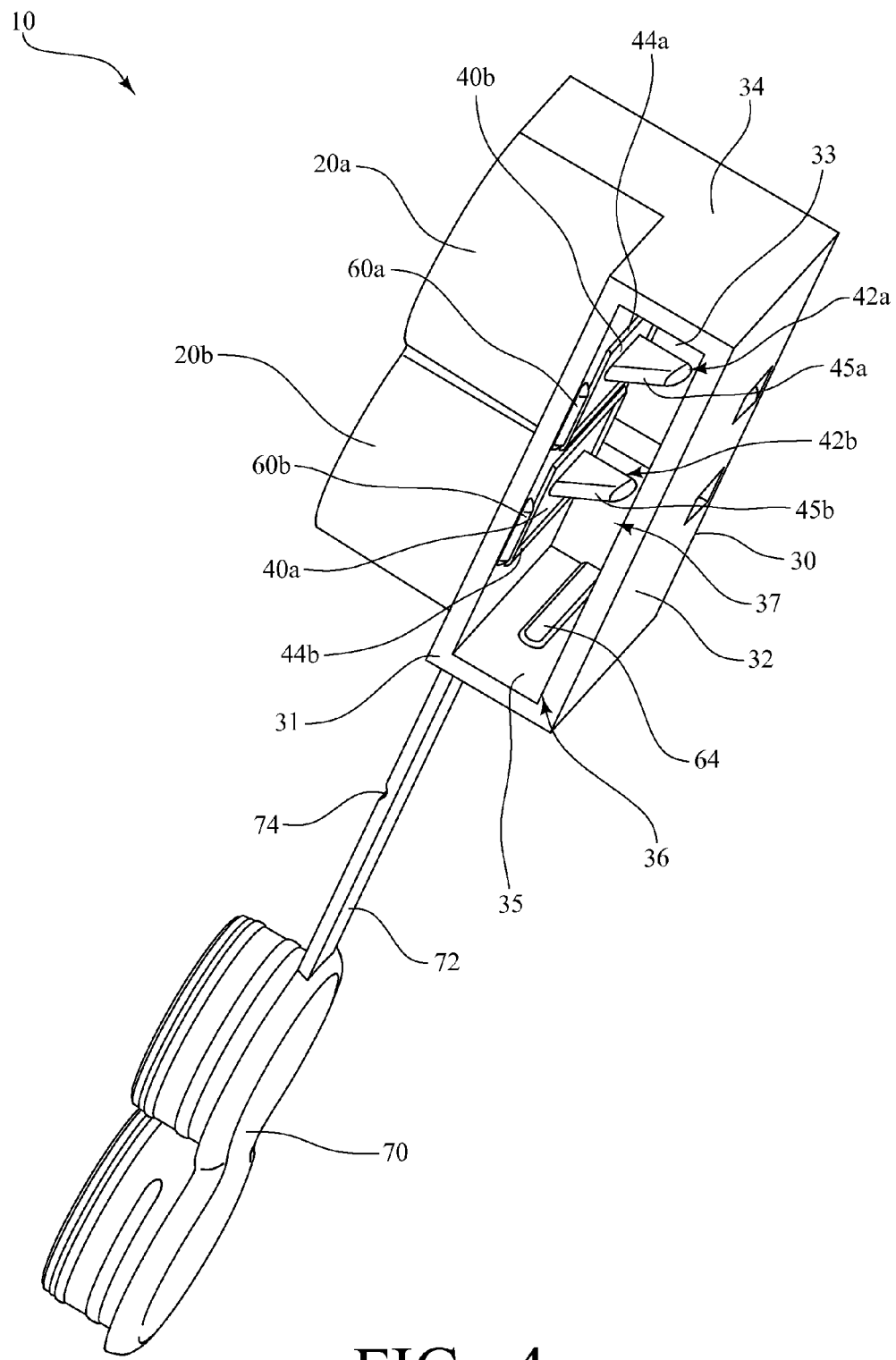
FIG. 4 is also another perspective view of the device shown in FIG. 1, but further illustrating the side of the device opposite that shown in FIG. 1.

To prevent the test cassette 50 from being prematurely inserted too far into the insertion area 37 of the housing 30 and prematurely contacting the ramps 42a, 42b on the doors 40a, 40b of the housing 30, and to also secure the test cassette 50 in the insertion area 37 of the housing 30, the housing 30 also includes a pair of stops 60a, 60b. Generally, the stops 60a, 60b are positioned on the top portion 31 of the housing 30 and extend downwardly into the insertion area 37 such that, upon insertion of the test cassette 50 in the housing 30, the stops 60a, 60b initially provide some resistance to the insertion of the test cassette 50. However, upon further insertion of the test cassette 50, the stops 60a, 60b then suitably engage a portion of the test cassette 50 to thereby secure the test cassette 50 within the housing 30 and prevent the test cassette 50 from falling out of the housing 30 during use. To further secure the test cassette 50 in the housing 30, and also prevent the test cassette 50 from being inserted too far into the housing 30 and prematurely contacting the ramps 42a, 42b, the housing 30 also includes a guide 64, only one of which is shown in FIG. 4, that is attached to each side wall 34, 35 of the housing 30.

In this regard, when the test cassette 50 is inserted in the insertion area 37 of the housing 30, the test cassette 50 also initially encounters some resistance from the guides 64, but, upon application of a slight amount of force, the test cassette 50 can then be slidably disposed into the guides 64 such that the guides 64 hold the test cassette 50 within a particular position in the insertion area 37 while the stops 60a, 60b are pushing against the test cassette 50 to thereby secure the test cassette 50 in the insertion area 37. Additionally, by completely inserting the test cassette 50 into the insertion area 37 along the guides 64, the guides 64 act to align the reaction wells 54a, 54b underneath the doors 40a, 40b. Once the reaction wells 54a, 54b of the test cassette are aligned underneath the doors 40a, 40b, upon opening the doors 40a, 40b into the cavities 26a, 26b of the reaction chambers 20a, 20b and placing the reaction chambers 20a, 20b in fluid communication with the insertion area 37, the reaction mixtures within the reaction chambers 20a, 20b can simply flow directly into the reaction wells 54a, 54b of the test cassette 50.

With further regard to the test cassette 50 itself, and referring now to FIGS. 5A-5B and FIG. 7, for use in the exemplary embodiment of the device 10 described above, each test cassette 50 generally includes a top cover 52, as shown in FIG. 5A, and a base 58 that is configured to attached to the top cover 52, as shown in FIG. 5B. Various means known to those of ordinary skill in the art can, of course, be used for attaching the base 58 of the test cassette 50 to the top cover 52 of the test cassette 50. In the exemplary test cassette 50 shown in FIGS. 5A-5B and FIG. 7, however, to attach the base 58 to the top cover 52 of the test cassette 50, the top cover 52 includes a series of posts 57 that can be inserted into a series of apertures 59 in the base 58 and used to attach (e.g., snap) the base 58 to the top cover 52.

Referring now to only FIG. 7, each test cassette 50 also includes a test strip 53 that is interposed between the top cover 52 and the base 58 prior to attaching the base 58 to the top cover 52. In this regard, when the test strip 53 is interposed between the base 58 and the top cover 52 and the base 58 and top cover 52 are attached to one another, the base 58 and the top cover 52 act to secure the test strip 53 in a desired position within the base. Various test strips known and routinely used by those of ordinary skill in the art for testing for an analyte of interest in a biological sample can be used in accordance with the present invention, and can be selected for a particular application depending on the particular analyte to be detected. In some embodiments, the test strips comprise an immunoassay test strip, such as those described in U.S. Pat. Nos. 6,406,922, 7,090,803, and 7,695,953, each of which is incorporated herein by this reference.

Regardless of the particular test strip utilized, however, and referring again to FIGS. 5A-5B and FIG. 7, the two reaction wells 54a, 54b are typically positioned at a distal end 51 of the top cover 52, such that each reaction well 54a, 54b can be aligned with each door 40a, 40b in the top portion 31 of the housing 30 upon placing the test cassette 50 in the insertion area 37 of the housing 30, as described further below. To facilitate the flow of the reaction mixture from the reaction chambers 20a, 20b through the doors 40a, 40b into the reaction wells 54a, 54b, the top cover 52 further includes a pair of bridges 55a, 55b, where each bridge 55a, 55b is positioned over a reaction well 54a, 54b to provide support for the ramp 42a, 42b upon insertion of the test cassette 50 into the insertion area 37. In this regard, instead of each ramp 42a, 42b falling into the reaction wells 54a, 54b when the test cassette 50 is inserted into the insertion area 37, the bridges 55a, 55b allow the ramps 42a, 42b to remain biased upward such that the reaction mixture can continue to flow into each reaction well 54a, 54b at a controlled rate upon the insertion of the cassette 50.

For example, to provide a device in which the reaction mixture flows from the wells at a desired rate, and referring now to FIGS. 8-10, in one exemplary embodiment, a device 210 for testing a biological sample is provided that includes a bridge 255a having a low height such that, upon insertion of the test cassette 250, the bridge 255a supports the ramp 242a and the door 240a of the housing 230 in a position where the door 240a is only opened slightly into the reaction chamber 220a and where only a minimal amount of reaction mixture is able to flow from the reaction chamber 220a at a given time. As another example, in another exemplary embodiment, a device 310 for testing a biological sample is provided that includes a bridge 355a having an intermediate height such that, upon insertion of the test cassette 350, the bridge 355a supports the ramp 342a and the door 340a of the housing 330 in a position where the door 340a is opened into the reaction chamber 320a in a manner that allows the reaction mixture to flow from the reaction chamber 320a at an intermediate rate. As yet another example, in yet another exemplary embodiment, a device 410 for testing a biological sample is provided that includes a bridge 455a having an increased height such that, upon insertion of the test cassette 450, the bridge 455a supports the ramp 442a and the door 440a of the housing 430 in a position where the door 440a is fully opened into the reaction chamber 420a to thereby allow the reaction mixture to flow from the reaction chamber 420a at faster rate. Of course, other devices that make use of test cassette bridges having various other heights are also contemplated to be within the spirit and scope of the present invention, and can be easily selected to provide a particular flow rate for a particular application.

Regardless of the particular flow rate provided for a particular application, and referring again to FIGS. 5A-5B and FIG. 7, once the reaction mixture flows from each reaction chamber 20a, 20b into the reaction wells 54a, 54b of the test cassette, the reaction mixtures are typically wicked up by the test strip 53. The test strip 53 then allows the reaction mixture to laterally flow along the test strip 53 such that the results of the particular test can be read and the amount of the analyte in the biological sample can be determined by analyzing the results of the test through windows 56a, 56b in the test cassette 50.

With further regard to the test cassettes of the present invention, it is appreciated that the number of reaction wells in a particular test cassette can also be varied and that test cassettes having various numbers of reaction wells can be provided for a particular application or for a particular device such that the number of reaction wells in the test cassette corresponds with the number of reaction chambers included in an exemplary device. For example, and referring now to FIGS. 6A-6B, in some embodiments, a test cassette is provided that, like the exemplary test cassette 50 shown in FIGS. 5A-5B and FIG. 7, includes a top cover 152 and a base 158 as well as a series of posts 157 and apertures 159 for connecting the top cover 152 to the base 158. However, unlike the test cassette 50, the top cover 152 only includes a single reaction well 154 for receiving a reaction mixture and a single window 156 for reading a test result. In other words, the test cassette formed by the attachment of the top cover 152 to the base 158 would be configured for use with a device of the present invention having only a single reaction chamber.

Finally, and referring again to FIGS. 1-4, each device 10 also includes a cap 70 for covering the open top 24a of the first chamber 20a and the open top 24b of the second chamber 20b. The cap 70 is connected to the housing 30 by a flexible arm 72, which includes a notch 74. The notch 74 is positioned in the flexible arm 72 such that bending the flexible arm 72 at the notch 74 allows the cap 70 to be aligned with the open top 24a of the first reaction chamber 20a and the open top 24b of the second reaction chamber 20b. Once the cap 70 is aligned with each open top 24a, 24b, the cap 70 can then be easily placed onto the reaction chambers 20a, 20b and secured to each reaction chamber 20a, 20b.

As described in further detail below, by securing the cap 70 to the reaction chambers 20a, 20b, the cap 70 provides a convenient means to cover each reaction chamber 20a, 20b and provide a closed environment to thereby facilitate the mixing and/or incubating of a biological sample and one or more reagents. Various means, including gaskets, threaded portions, and the like, can, of course, be included on the cap 70 to secure the cap 70 to the reaction chambers 20a, 20b. In some embodiments, and as shown in FIGS. 1-4, the cap 70 of the device 10 includes raised portions 75, 77 that are configured to matingly engage corresponding depressions 76, 78 defined by the interior walls 22a, 22b of the reaction chambers 20a, 20b to thereby secure the cap 70 to the reaction chambers 20a, 20b.

Referring now to FIG. 11, further provided by the present invention are methods for testing a biological sample for an analyte of interest. In this exemplary implementation, and as indicated by block 500, the testing commences by providing a device for testing a biological sample that includes a reaction chamber having an interior wall defining an open top and a cavity for receiving a reaction mixture; a housing positioned below the reaction chamber, and having a top portion, a bottom portion, a back wall, and two opposing side walls defining an open end and an insertion area for receiving a test cassette; and a door that is positioned in the top surface of the housing and includes a ramp that extends downwardly into the insertion area.

Subsequent to providing the device, a biological sample and one or more reagents are placed into the cavity of each reaction chamber to thereby create a suitable reaction mixture, as indicated by block 510. With regard to the biological samples used in accordance with the present invention, the biological sample can include any body fluid or tissue in which an analyte of interest can be detected, including, but not limited to, blood, plasma, serum, urine, or oral fluid samples. In some embodiments, for example, the biological sample is an oral fluid sample, such as a saliva sample.

Typically, the one or more reagents include a suitable buffer solution and a suitable identifying reagent that is capable of targeting a particular analyte of interest, such as a drug of abuse. For example, in certain embodiments, a buffer solution that assists in the removal or reduction of interferents that may potentially interfere with the detection of the analyte of interest can be used along with a gold particle attached to a suitable antibody or antigen that is used to target the particular analyte of interest, as described in U.S. Pat. No. 7,695,953. In certain embodiments of the present invention, where the analyte of interest is a drug, such as a drug of abuse, the drugs targeted by the antibody or antigen can be any drug or other compound of interest that can be detected in a biological sample. Such drugs include, but are not limited to, amphetamines, benzodiazepines, cocaine, methadone, methamphetamines, phencyclidine (PCP), and tetrahydrocannabinol (THC). In some embodiments, and as also described in U.S. Pat. No. 7,695,953, a gold-labeled antibody specific to the target drug can be provided in the reaction chamber, e.g., in dry form, prior to the addition of the buffer solution and biological sample to the reaction chamber.

Once the biological sample and the one or more reagents are added to the cavity of the reaction chamber of the device, the biological sample and the reagents are generally mixed together, as indicated by block 520, and allowed to incubate for a suitable time period such that the identifying reagent has sufficient time to target and bind to the analyte of interest. In certain embodiments, to promote the mixing of the reagents and/or to promote the breakdown of any interfering molecules, the device can be slightly shaken or otherwise agitated by gently moving the device from side to side on a flat surface. In other embodiments, the cap of the devices is used to cover the open tops of the reaction chambers such that more vigorous shaking can be used to mix the reaction mixtures as needed. In yet further embodiments, the biological sample can be mixed with a suitable buffer solution prior to placing the biological sample and buffer mixture into the reaction chamber and combining it with the reagents (e.g., reagents that are provided in a dried form in the reaction chamber).

Once the biological sample and the reaction mixtures have been mixed, and following a suitable incubation period, an immunoassay test cassette, which includes a test strip specific for the analyte to be detected, is inserted into the insertion area of the device, as indicated by block 530. In inserting the immunoassay test cassette into the insertion area, the test cassette is first pushed past the stops included in the top portion of the housing of the device and is inserted along the guides in each opposing side wall to thereby secure the cassette in the housing and to align the reaction wells of the cassette with the doors included in the top portion of the housing. In this regard, as the test cassette is pushed into the insertion area of the housing, the test cassette initially begins to encounter the angled front edge of the ramps extending downwardly from the doors. As the test cassette then moves further inward, the triangular shape of the ramp progressively engages the test cassette and the perimeter portion of the door eventually breaks away from the remainder of the top portion of the housing and allows the doors to be opened into the reaction chamber. The upward movement of the door into the reaction chamber then allows the reaction mixture to flow downward through the doors into the reaction wells of the test cassette and onto the test strip that is interposed between the top cover and the base of the test cassette.

Once the reaction mixture flows down into reaction wells and onto the test strip, the reaction mixture is then wicked up by the test strip and laterally flows along the test strip such that the results of the test can be read and the amount of analyte in the biological sample can be determined by analyzing the results of the test through the windows of the test cassette, as indicated by block 540. In some implementations of the methods for testing a biological sample for an analyte of interest, determining an amount of an analyte of interest, such as a drug of abuse, in a biological sample can include only a qualitative assessment of the presence or absence of the analyte of interest in the biological sample. In other implementations of the methods of the present invention, however, a quantitative assessment of the amounts of the analyte of interest in the biological sample can be made. Such quantitative assessments can be made by various techniques known to those of ordinary skill in the art.

The above-described devices and methods for testing a biological sample that make use of a reaction chamber and a housing, which are capable of being placed in fluid communication with one another, thus provide a convenient platform for mixing, incubating, and depositing a reaction mixture onto test strip in a test cassette, with the added benefit that the reaction chambers and housing allow for a controlled release of a reaction mixture onto a test cassette in a manner that provides a quick and accurate testing for drugs of abuse or other analytes of interest.

One of ordinary skill in the art will recognize that additional embodiments are also possible without departing from the teachings of the presently-disclosed subject matter. This detailed description, and particularly the specific details of the exemplary embodiments disclosed herein, is given primarily for clarity of understanding, and no unnecessary limitations are to understood therefrom, for modifications will become apparent to those skilled in the art upon reading this disclosure and may be made without departing from the spirit or scope of the presently-disclosed subject matter.

What is claimed is:

1. A device for testing a biological sample, comprising:
    a reaction chamber having an interior wall defining an open top and a cavity for receiving a reaction mixture;
    a housing positioned below the reaction chamber, the housing having a top portion, a bottom portion, a back wall, and two opposing side walls defining an open end and an insertion area for receiving a test cassette; and
    a door positioned in the top portion of the housing and including a ramp downwardly extending into the insertion area such that biasing the ramp upwards opens the door into the cavity of the reaction chamber and places the reaction chamber in fluid communication with the insertion area.

2. The device of claim 1, wherein the door includes a perimeter portion configured to separate from the top portion of the housing upon biasing the ramp upwards.

3. The device of claim 1, wherein a front edge of the ramp is angled away from the open end of the housing.

4. The device of claim 1, further comprising a stop positioned on the top portion of the housing and extending downwardly into the insertion area, the stop for securing the test cassette in the insertion area.

5. The device of claim 1, further comprising a guide attached to each side wall of the housing for aligning the test cassette in the insertion area.

6. The device of claim 1, wherein the test cassette comprises:
    a top cover defining a reaction well for receiving the reaction mixture from the reaction chamber and further defining a window for reading a test result;
    a base configured to attach to the top cover; and
    a test strip interposed between the top cover and the base.

7. The device of claim 6, wherein the reaction well is positioned on the top cover such that the reaction well is aligned with the door upon placing the test cassette into the insertion area.

8. The device of claim 6, wherein the top cover includes a bridge positioned across the reaction well, the bridge for supporting the ramp upon placing the test cassette into the insertion area.

9. The device of claim 1, further comprising a cap for covering the open top of the reaction chamber.

10. The device of claim 9, wherein the cap is connected to the housing by a flexible arm.

11. The device of claim 10, wherein the flexible arm includes a notch positioned in the flexible arm such that bending the flexible arm at the notch allows the cap to be aligned with the open top of the reaction chamber.

12. The device of claim 9, wherein the cap includes a means for securing the cap to the reaction chamber.

13. A device for testing a biological sample, comprising:
a first reaction chamber and a second reaction chamber, each reaction chamber having an interior wall defining an open top and a cavity for receiving a reaction mixture;
a housing positioned below the first reaction chamber and the second reaction chamber, the housing having a top portion, a bottom portion, a back wall, and two opposing side walls defining an open end and an insertion area for receiving a test cassette; and
a pair of doors positioned in the top portion of the housing, each door including a ramp downwardly extending into the insertion area such that biasing the ramp upwards opens the door into the cavity of each reaction chamber and places each reaction chamber in fluid communication with the insertion area.

14. The device of claim 13, wherein each door includes a perimeter portion configured to separate from the top portion of the housing upon biasing each ramp upwards.

15. The device of claim 13, wherein a front edge of each ramp is angled away from the open end of the housing.

16. The device of claim 13, further comprising a pair of stops positioned on the top portion of the housing and extending downwardly into the insertion area, the stops for securing the test cassette in the insertion area.

17. The device of claim 13, further comprising a guide attached to each side wall of the housing for aligning the test cassette in the insertion area.

18. The device of claim 13, wherein the test cassette comprises:
a top cover defining two reaction wells for receiving each reaction mixture from each reaction chamber and further defining two windows for reading test results;
a base configured to attach to the top cover; and
at least one test strip interposed between the top cover and the base.

19. The device of claim 18, wherein the two reaction wells are positioned on the top cover such that each reaction well is aligned with each door in the top portion of the housing upon placing the test cassette into the insertion area.

20. The device of claim 18, wherein the top cover includes a bridge positioned across each reaction well, each bridge for supporting the ramp upon insertion of the test cassette into the insertion area.

21. The device of claim 13, further comprising a cap for covering the open top of the first reaction chamber and the open top of the second reaction chamber.

22. The device of claim 21, wherein the cap is connected to the housing by a flexible arm.

23. The device of claim 22, wherein the flexible arm includes a notch positioned in the flexible arm such that bending the flexible arm at the notch allows the cap to be aligned with the open top of the first reaction chamber and the open top of the second reaction chamber.

24. A method for testing a biological sample for an analyte of interest, comprising:
providing a device, including:
a reaction chamber having an interior wall defining an open top and a cavity for receiving a reaction mixture;
a housing positioned below the reaction chamber, the housing having a top portion, a bottom portion, a back wall, and two opposing side walls defining an open end and an insertion area for receiving a test cassette; and
a door positioned in the top portion of the housing and including a ramp downwardly extending into the insertion area such that biasing the ramp upwards opens the door into the cavity of the reaction chamber and places the reaction chamber in fluid communication with the insertion area;
placing the biological sample and one or more reagents into the cavity to thereby create the reaction mixture;
inserting an immunoassay test cassette into the insertion area such that the test cassette biases the ramp upwards and opens the door into the cavity of the reaction chamber to allow the reaction mixture to contact an immunoassay test strip; and
determining an amount in the biological sample of the analyte of interest.

25. The method of claim 24, wherein the biological sample comprises blood, plasma, serum, urine, or saliva.

26. The method of claim 24, wherein the biological sample comprises saliva.

27. The method of claim 24, further comprising the step of mixing the biological sample and the one or more reagents after placing the biological sample and the one or more reagents into the cavity.

28. The method of claim 24, further comprising the step of covering the open top of the cavity after placing the biological sample and the one or more reagents into the cavity.

29. The method of claim 24, wherein the analyte of interest is a drug of abuse.

30. The method of claim 29, wherein the drug of abuse is selected from the group consisting of amphetamines, benzodiazepines, cocaine, methadone, methamphetamines, phencyclidine, and tetrahydrocannabinol.

31. A device for testing a biological sample, comprising:
a reaction chamber having an interior wall defining an open top and a cavity for receiving a reaction mixture;
a housing positioned below the reaction chamber, the housing having a top portion, a bottom portion, a back wall, and two opposing side walls defining an open end and an insertion area for receiving a test cassette;
a door positioned in the top portion of the housing and including a ramp downwardly extending into the insertion area such that biasing the ramp upwards opens the door into the cavity of the reaction chamber and places the reaction chamber in fluid communication with the insertion area; and
a test cassette.

* * * * *